United States Patent
Franetzki

[11] Patent Number: 5,833,684
[45] Date of Patent: Nov. 10, 1998

[54] HANDPIECE FOR A STOMATOLOGICAL APPLICATION FOR LASER LIGHT

[75] Inventor: Manfred Franetzki, Bensheim, Germany

[73] Assignee: Sirona Dental Systems GmbH & Co. KG, Bensheim, Germany

[21] Appl. No.: 142,832

[22] Filed: Oct. 25, 1993

Related U.S. Application Data

[63] Continuation of Ser. No. 913,627, Jul. 16, 1992, abandoned.

[30] Foreign Application Priority Data

Jul. 17, 1991 [DE] Germany ............. 41 23 729.3

[51] Int. Cl.⁶ ......................................... A61B 17/39
[52] U.S. Cl. ....................... 606/17; 606/18; 606/16
[58] Field of Search ............... 606/2, 10, 13–18; 607/88, 89; 604/22, 21

[56] References Cited

U.S. PATENT DOCUMENTS

| | | | |
|---|---|---|---|
| 3,821,510 | 6/1974 | Muncheryan | 128/395 |
| 3,834,391 | 9/1974 | Block | 606/16 |
| 3,865,113 | 2/1975 | Sharon et al. | |
| 4,608,980 | 9/1986 | Aihara | 606/16 |
| 4,638,800 | 1/1987 | Michel | 606/18 |
| 4,694,828 | 9/1987 | Eichenbaum | 606/6 |
| 4,826,431 | 5/1989 | Fujimura | 606/14 |
| 4,849,859 | 7/1989 | Nagasawa | 606/16 |
| 5,020,995 | 6/1991 | Levy | |
| 5,151,097 | 9/1992 | Daikuzon | 606/16 |

FOREIGN PATENT DOCUMENTS

| | | |
|---|---|---|
| 0 073 617 | 3/1983 | European Pat. Off. |
| 37 13 512 | 10/1987 | Germany |
| WO 89/08432 | 9/1989 | WIPO |
| WO 90/01907 | 3/1990 | WIPO |

*Primary Examiner*—Michael Peffley
*Attorney, Agent, or Firm*—Hill & Simpson

[57] ABSTRACT

A handpiece for stomatological application of laser light includes a movable light and agent transmission system connected to a proximal side of the handpiece and an application element containing a work tip connected to a distal side of the handpiece. Advantageously, the laser beam in the application element is directed onto an exit location that proceeds essentially transversely with respect to the longitudinal axis of the application element, and is focused such that the focus of the laser light lies immediately in front of a light exit window.

12 Claims, 4 Drawing Sheets

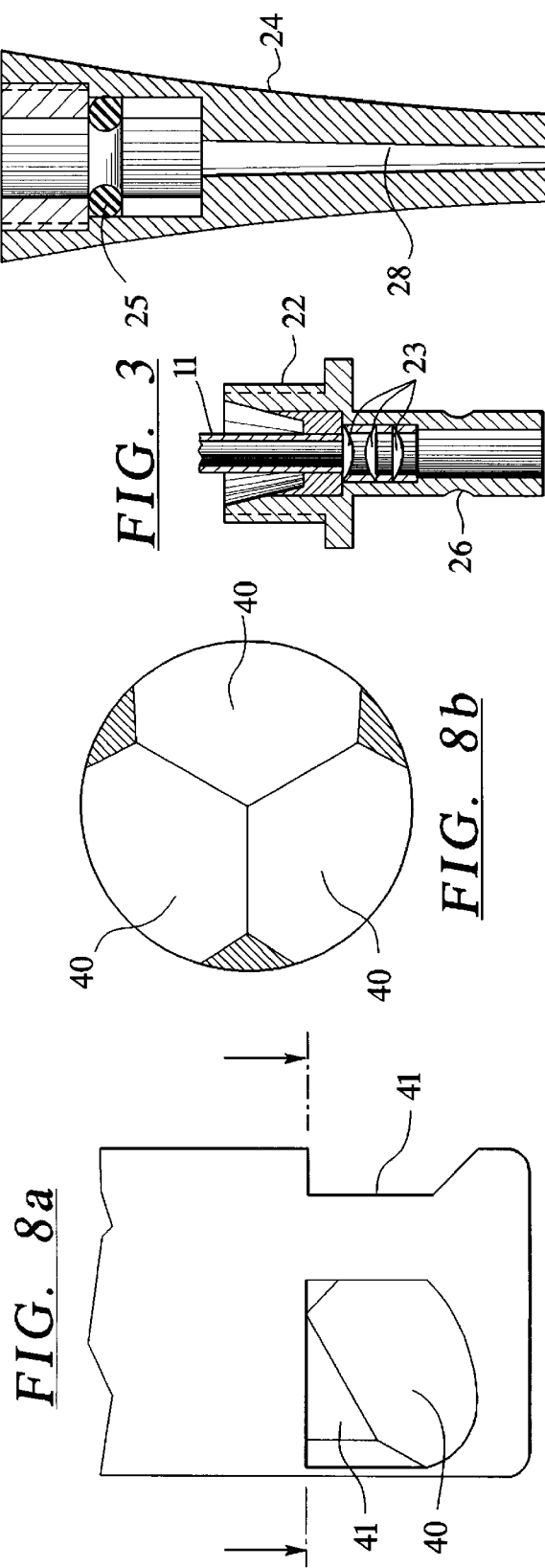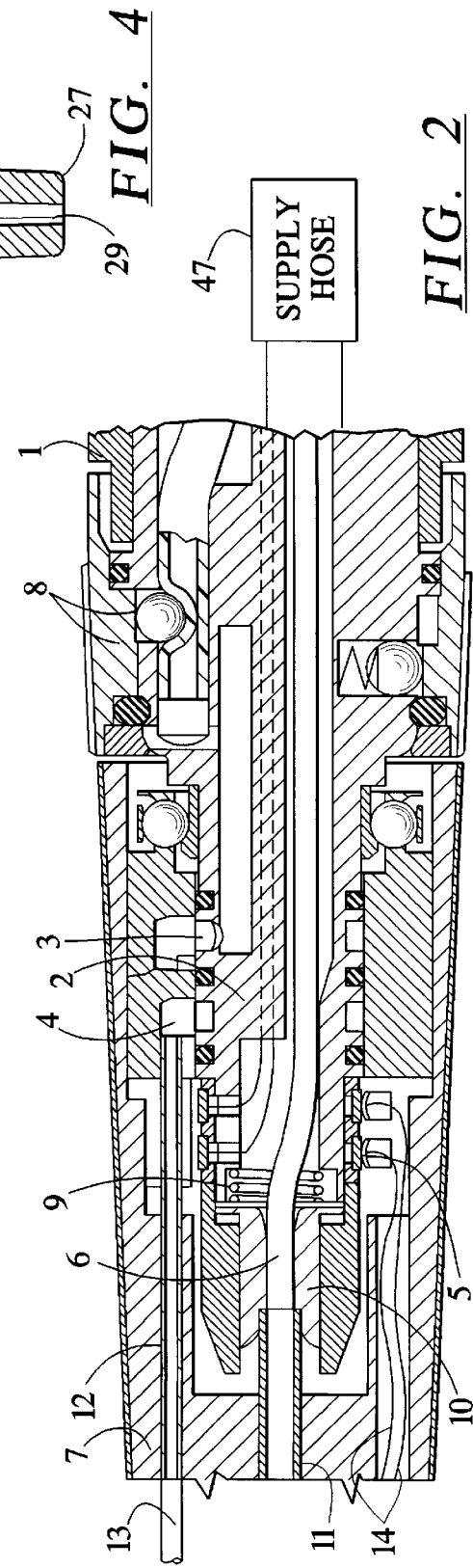

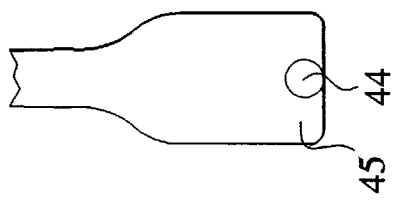
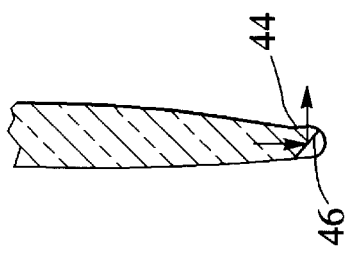
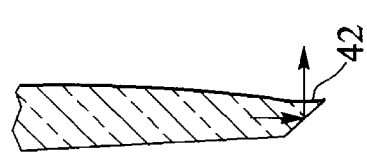
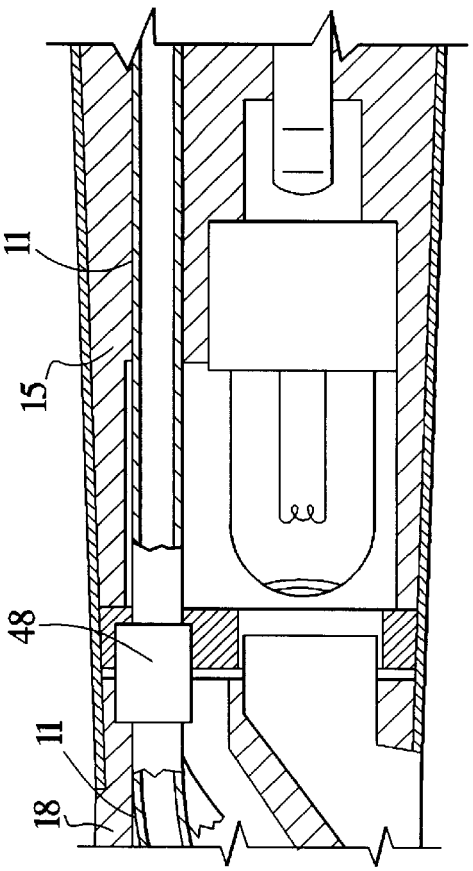
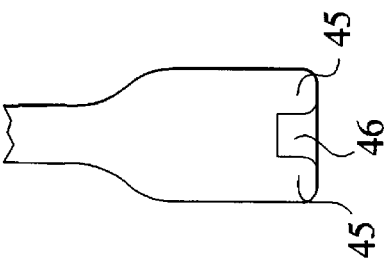
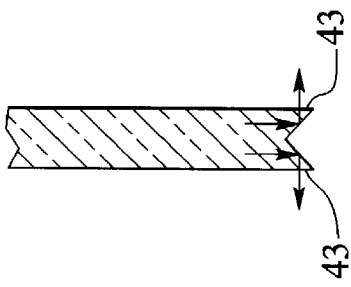

HANDPIECE FOR A STOMATOLOGICAL APPLICATION FOR LASER LIGHT

This is a continuation of application Ser. No. 07/913,627, filed Jul. 16, 1992, (now abandoned).

FIELD OF THE INVENTION

The present invention relates generally to a handpiece for stomatological application of laser light, and particularly to such handpieces as used for eroding hard dental substances.

BACKGROUND OF THE INVENTION

Various laser systems are known that are suitable for use in dental treatment. Examples of such systems are discussed in U.S. Pat. Nos. 3,865,113 and 3,821,510, German OS 3 713 512; and PCT Publications WO-US 89/00984 and WO-US 89/03825. Such known arrangements typically employ handpieces having tips from which the laser light emerges. The laser light is ordinarily deflected at least once in the handpiece tip, then emerges either as a free beam or with an optically conductive applicator. The beam travels straight from the tip to the tooth to be treated, requiring manipulation of the laser tool that is similar to that which would be required if one were drilling a tooth with a cylindrical drill that had its bit extending axially from an end face of the drill.

However, dental drills are not axially constructed, as are known laser systems. Typically, the drilling portions of dental drills are angularly offset from the handpieces. Since the construction of known laser handpieces differs markedly from typical dental tools, dental practitioners must undergo extensive retraining to effectively use laser systems. Even with sufficient training, certain procedures (such as work on lateral walls and specific undercuts in cavities) are almost impossible to perform with known laser systems, due to the difficulty of handpiece manipulation. Further, known laser systems cannot achieve smooth surfaces and sharp contours by performing dental procedures with a free laser beam. Moreover, a risk of unintentional injury of the patient is present when using the known laser systems.

SUMMARY OF THE INVENTION

It is an object of the present invention to provide a handpiece for use in a laser system that enables the user to perform dental procedures in a patient's mouth in the manner to which the user is accustomed with non-laser systems. In a handpiece constructed in accordance with the principles of the present invention, the laser light can be concentrated on a procedure location to be handled with the handpiece. Further, care must be exercised to see that the procedure location is supplied with a suitable coolant, such as water or spray, and that the work area is appropriately illuminated, during the procedure.

These and other objects are achieved in a handpiece for stomatological application of laser light having a proximal side connected to both a movable light and an agent transmission system, and a distal side ending in an application element, where the application element contains a work tip.

A handpiece constructed in accordance with the principles of the present invention is particularly advantageous in that the handpiece allows procedures to be carried out that are similar to procedures carried out with conventional instruments, such as conventional hand drills and angle drills.

BRIEF DESCRIPTION OF THE DRAWINGS

FIG. 2 illustrates a front sectional view of a handpiece back joined to a connection armature;

FIG. 3 illustrates a front sectional view of an alternative embodiment for a carrier provided for attaching an application element, as illustrated in FIG. 1;

FIG. 4 illustrates a first exemplary embodiment of an application element;

FIGS. 5–11 illustrate alternative embodiments of an application element; and

FIG. 12 illustrates a front sectional view of a second exemplary embodiment of a handpiece front constructed in accordance with the principles of the present invention.

DESCRIPTION OF THE PREFERRED EMBODIMENTS

Figure 1:
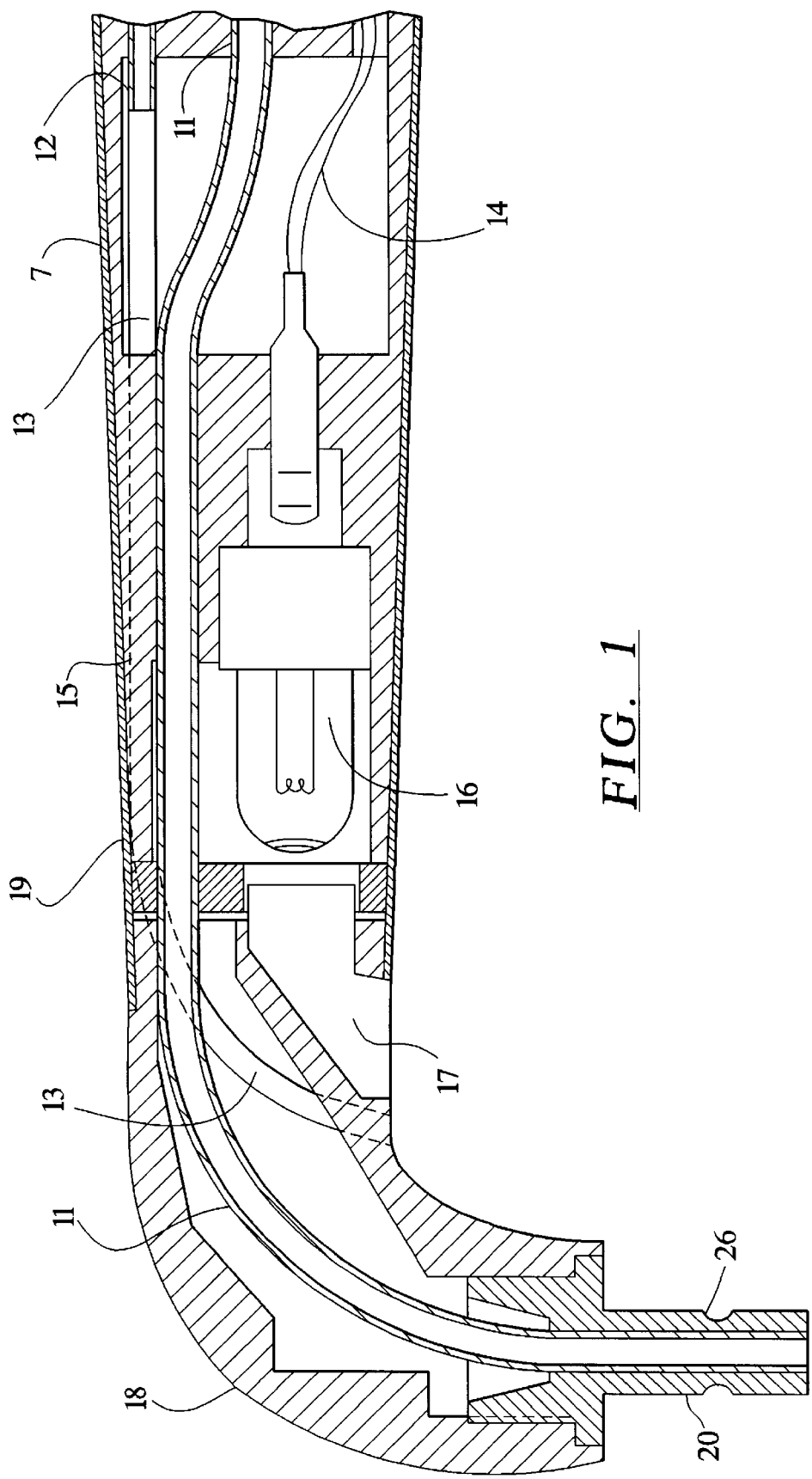
FIG. 1 illustrates a front sectional view of a first exemplary embodiment of a handpiece front constructed in accordance with the principles of the present invention.

A handpiece constructed in accordance with the principles of the present invention is set forth in detail with respect to FIGS. 1 and 2. FIG. 1 illustrates the front section, and FIG. 2 illustrates the back section of the handpiece of the present invention connected to a connector part.

As illustrated in FIG. 2, a supply hose 45 (not illustrated in detail) is provided for transmitting air, water, electricity and light through suitable lines to a connection armature 1. The connection armature 1 is designed as a rotating joint in a manner known to one of ordinary skill in the art. The connection armature 1 also contains a peg-shaped coupling part 2 through which water, air, electricity and light are transmitted from the connecting armature 1 onto the handpiece 7 by means of lines and channels 3 through 6 in a manner known to one of ordinary skill in the art. A metering device 8 is inserted into the water feed line, and regulates the flow of water by pinching a feeder hose. Providing air and water for cooling the procedure location are accomplished in a way known to one of ordinary skill in the art of constructing standard drill handpieces, and therefore, is not discussed in greater detail herein.

A light conductor 6 is provided for transmitting laser light generated by an externally arranged laser light generator. The light conductor 6 ends at a face end of the coupling part 2 in an axially movable connector part 10. The axially movable connector part 10 is biased axially by a compression spring 9. As the laser light proceeds through the handpiece, it is guided with a light conductor arranged in a jacket tube. The light conductor engages the face end of the light conductor 6 when the handpiece 7 is attached to the connecting armature 1 in a way that ensures light transmission.

The connecting part 10 can also be arranged at its end face in order to provide easier coupling. Optical losses at the light coupling location are avoided, or kept to a minimum, by providing at least one end face of the light guide end with a medium of good optical conductivity. Such a medium can include, for example, a suitable fluid provided at one end of the light guide end prior to coupling.

As illustrated in FIG. 1, a light conductor 11 and leads 12 through 14 for providing air, water and power, are held respectively in a base part 15 lead 13 is arranged parallel to lead 12. An incandescent lamp 16 is provided, and is connected to slip rings 5 in the connecting armature 1 by leads 14. The incandescent lamp 16, held in the base part 15, is provided for illuminating the procedure location. The incandescent lamp 16 provides light to optics 17 that guides the light onto the preparation location. A head housing 18 is angled at approximately 90° relative to the longitudinal axis of the handpiece 7. The head housing 18 is connected to the base part 15 of the handpiece 7 in a suitable manner. Advantageously, the head housing 18 can be releasably connected to the base part 15 by a suitable snap-in connection. A suitable separating coupling for the light conductor would then also be provided at the parting location. Further, a gripping sleeve 19 that surrounds the base part 15 can be arranged so as to be removable from the base part 15. Thus, both the head housing 18 and gripping sleeve 19 could, for example, be readily separated from the base part 15 for sterilization purposes.

The application elements illustrated in FIGS. 4–11 can be alternatively attached to a carrier 20, disposed at a free end of the light conductor 11. The carrier 20 is attached by a suitable fastener, such as a screw, at the face end of the head housing 18, and can be readily interchanged when necessary. Thus, the free end of the light conductor 11 can be selectively arranged with respect to the free end of the carrier 20.

A suitable light conductor to be used within the handpiece 7 can include, for example, a flexible or rigid hollow tube that is either polished or coated on the inside. Such a suitable light conductor can be selected independent of the wavelength of the laser source provided. Also, the light conductor used within the handpiece 7 can be a rigid or flexible optical fiber including a material that is transmissive for the associated wavelength of the laser source. For example, silica glass can be used advantageously for wavelengths in the range of 250 nm through approximately 2.7 $\mu$m. Further, for example, ZrF or a silver halogenoid can be used for wavelengths above approximately 2.5 $\mu$m. Additionally, liquid-filled waveguides can provide suitable light conductors to be used within the handpiece.

As illustrated in FIG. 1, the light conductor 11 can be arranged at the free end of the carrier 20. Alternatively, as illustrated in FIG. 3, carrier 22 is provided, having an optics 23 is arranged at the free end of the light conductor 11. The optics 23 is joined to the free end of the light conductor 11, and focuses the laser light.

A variety of application elements can be alternatively arranged on one of the carriers 20, 22. As illustrated in FIG. 4, a first application element 24 can be rotatably latched and readily removable at, for example, the carrier 21 with an O-ring connection 25, 26. In accordance with the principles of the present invention, any suitable catch element can be provided. For example, in addition to an O-ring connection having a certain friction lock that is desirable under certain circumstances, a lock washer or other suitable catch element can also be provided.

The application element 24 includes a hollow channel 28 that is mirrored on the inside and conically tapered toward a work tip 27. The hollow channel 28 accepts laser light from the light conductor 11 and allows it to emerge at a light exit window 29. A glass rod that forms a central light exit window at the work tip, or any other suitable channel, can be provided in place of the hollow channel 28.

The work tip of the application element, as illustrated in FIG. 4, can be designed such that the focus of the light radiation is formed outside and immediately in front of the light exit window 29 of the application element 24. Alternatively, an arrangement in which the laser light diverges from the light exit window 29 can be provided. Where the laser light diverges when conducted from the light exit window 29, the greatest energy density is directly in the plane of the exit window 29. For example, focusing immediately in front of the light exit window 29 can be achieved by providing a mirroring back wall or by providing a lens in the exit window 29, as illustrated below.

Thus, the present invention provides a laser handpiece with which contact work can proceed in the same manner as with a commercially available drill instrument. That is, a handpiece constructed in accordance with the principles of the present invention is operated with tactile feedback in the immediate proximity of the tip. Due to the nature of the light being passed, the divergent light energy drops rapidly outside the tip, such that damage to the surrounding procedure location is prevented.

Figure 7A:
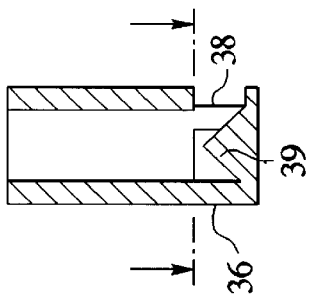
Figure 7B:
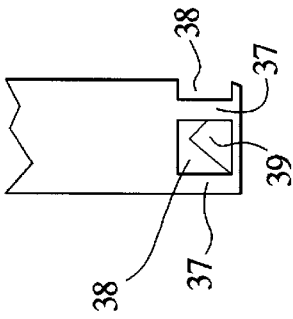
Figure 7C:
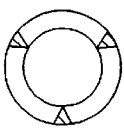
Figure 6A:
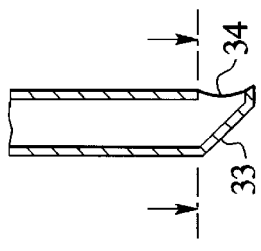
Figure 6B:
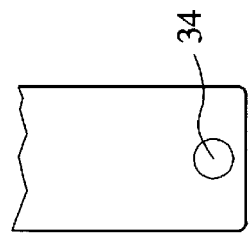
Figure 6C:
Figure 5A:
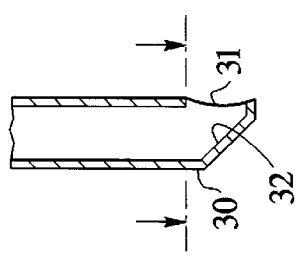
Figure 5B:
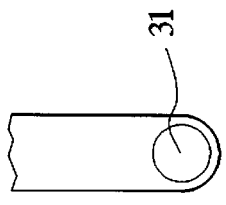
Figure 5C:

FIGS. 5–7 illustrate three alternative embodiments for the work tips (the lower portion of the application element). These Figures illustrate respective longitudinal sections, FIGS. 5a, 6a, 7a, a view onto the light exit location therebelow, and cross sections along the line in the region of the light exit location indicated by arrows, FIGS. 5c, 6c, 7c. These three embodiments each include waveguides that are coated (mirrored) or polished on the inside. The work tip 30 illustrated in FIG. 5, includes a light exit location 31, arranged transversely relative to the longitudinal axis, that is suitable for processing the preparation location at the lateral side. The laser light is deflected at an oblique surface 32. The oblique surface 32-can advantageously include optical properties such that the oblique surface 32 focuses the laser light at the deflection location onto a procedure area situated at or immediately in front of the exit location. As illustrated in FIG. 6, the work tip 33 is designed for a lateral laser light exit. In contrast to the embodiment illustrated in FIG. 5, small, wing-like guide lugs 35 are arranged at both sides of the light exit window 34. In this arrangement, once the tip has been arranged on the processing surface, the light exit opening is always aligned in the direction of the processing surface when sliding along the processing surface. For example, a dental cavity or a crown stump can be continually processed in this manner without manually readjusting the opening or exit window.

FIG. 7 illustrates a work tip 36 designed to provide a laterally emerging laser light beam that is virtually uniform over the entire circumference of the light beam. The light exit is interrupted only at retaining webs 37. With such a work tip, dental procedures can be performed in substantially the same manner as with a rotating drill instrument. However, this embodiment requires the use of a more powerful laser light source than set forth with respect to the above embodiment. A conical prism 39 is provided for focusing or deflecting the light from the hollow channel onto the light exit window 38. The prism 39 can be selected to have characteristic properties that focus the light, and can be of any suitable geometry for focusing and deflecting the light from the hollow channel.

FIG. 8 illustrates an embodiment wherein deflection of the laser light occurs by means of three mirrors 40 arranged to form a tetrahedron that direct the laser light onto the light exit window 41. FIG. 8a illustrates a longitudinal section of the embodiment. FIG. 8b illustrates a cross section along the line in the region of the light exit location indicated by arrows.

FIGS. 9–11 illustrate various work tips constructed in a similar manner to the work tips set forth above. However, in the work tips of FIGS. 9–11, the light can emerge only at the desired opening, i.e., the exit window. In these embodiments, the entire application element is composed of a solid material that allows the laser light to pass, and the surfaces are mirrored (except for the light exit location). In order to provide work tips wherein the light can emerge only at the exit window, the light is cast back into the material of the tip at the other surfaces, as a result of a total reflection or, as illustrated, by reflection at a mirrored surface. The light exit windows 42 through 44 can be substantially planar.

As illustrated in FIG. 10, a work tip can be provided wherein the retaining webs of FIGS. 7 and 8 are omitted.

As illustrated in FIG. 11, a work tip 60 containing wing-like guide elements 45 arranged at both sides of the exit window is provided, as in FIG. 6. The oblique surface 46 that guides the laser light is also mirrored at the outside of the surface. FIG. 11a illustrates a longitudinal section of the work tip. FIG. 11b illustrates a cross section along the lines in the regions of the light exit location indicated by arrows. FIGS. 11c and 11d illustrate a front view onto the light exit location and a back view onto the light exit location, respectively.

As illustrated in FIG. 12, the head housing 18 can be releasably connected to the base part 15 by a suitable snap-in connection. A suitable separating coupling, such as coupling 48 is provided at the optical parting location.

Although the light exit in the above embodiments is defined as being axial or radial, the present invention contemplates that the geometry of the light exit can include all possible geometries, wherein the light beam can emerge between the two previously-mentioned positions.

In all embodiments of the work tips set forth hereinabove, the light exit opening can be point-shaped or slot-shaped, where the lateral design is especially advantageous for processing a crown stump.

Further, the procedure location can be cooled in a manner known for conventional drill instruments. The agents of air and/or water required for this purpose are supplied to the work tip of the application element in a suitable manner, as would be apparent to those of skill in the art.

Although various minor modifications may be suggested by those versed in the art, it should be understood that I wish to embody within the scope of the patent granted hereon all such modifications as reasonably and properly come within the scope of my contribution to the art.

I claim:

1. A hand-held dental treatment apparatus for use with a source of laser light for stomatological application of said laser light to a dental treatment location, comprising:

a handpiece having a proximal end and a distal end with a longitudinal axis extending between said proximal and distal ends, said distal end having a distal end axis disposed approximately 90° relative to said longitudinal axis and terminating in a distal surface;

light transmission means connectable to said source of laser light for conducting said laser light through said handpiece in a propagation path along said longitudinal axis and said distal end axis;

carrier means for focussing said laser light to said dental treatment location, oriented perpendicularly relative to said longitudinal axis of said handpiece, said carrier means having a first end mating with said distal surface, a second end spaced from said first end and a central axis between said first and second ends, with said light transmission means extending through said carrier means along said central axis, said second end being oriented relative to said longitudinal axis to be perpendicular to said dental treatment location when said handpiece is held by a user, a light exit port, said carrier means including optical deflector means, optically coupled to said light transmission means and disposed between said first and second ends, for optically deflecting said laser light and for causing said laser light to exit said carrier means through said light exit port in a direction perpendicular to said central axis and parallel to said second end, and said carrier means focussing said laser light to said dental treatment location immediately in front of said light exit port.

2. A hand-held dental apparatus as claimed in claim 1 wherein said carrier means has an outer surface disposed substantially parallel to said central axis, and wherein said light exit port comprises a light exit window disposed in said outer surface.

3. A hand-held dental apparatus as claimed in claim 1 further comprising means for rotatably connecting said first end of said carrier means to said distal surface, and wherein said light transmission means includes a light conductor extending along said longitudinal axis and said distal end axis and terminating at said distal surface.

4. A hand-held dental apparatus as claimed in claim 3 wherein said means for rotatably connecting said first end of said carrier means to said distal surface comprises means for detachably rotatably connecting said first end of said carrier means to said distal surface.

5. A hand-held dental apparatus as claimed in claim 3 wherein said means for rotatably connecting said first end of said carrier means to said distal surface includes means for focusing said laser light to a focus in the region of said light exit means.

6. A hand-held dental apparatus as claimed in claim 1, wherein said carrier means comprises a light waveguide.

7. A hand-held dental apparatus as claimed in claim 1 wherein said carrier means further comprises guide means, disposed at said second end of said carrier means and adapted to slide along a surface in the region of said application zone, for automatically aligning said light exit means relative to said surface in the region of said application zone.

8. A hand-held dental apparatus as claimed in claim 1 wherein said carrier means comprises a solid element transmissive for said laser light.

9. A hand-held dental apparatus as claimed in claim 1 wherein said optical deflector means comprises a work tip of said carrier means having reflective interior surfaces therein for reflecting said laser light and focusing said laser light immediately in front of said light exit port.

10. A hand-held dental apparatus as claimed in claim 1 for use with a fluid source, and further comprising:

supply hose means, connected to said fluid source and extending through said handpiece, for delivering fluid from said fluid source to a location in the region of said dental treatment location.

11. A hand-held dental apparatus as claimed in claim 1 further comprising:

rapid-action coupling means for connecting said light transmission means to said source of laser light.

12. A hand-held dental apparatus as claimed in claim 1 further comprising a source of illuminating light disposed in said handpiece, and optical means for directing illuminating light from said source of illuminating light to a location in the region of said dental treatment location.

* * * * *